US00PP15778P2

(12) United States Plant Patent
Vandenberg

(10) Patent No.: US PP15,778 P2
(45) Date of Patent: May 31, 2005

(54) *CHRYSANTHEMUM* PLANT NAMED 'ZIP'

(50) Latin Name: *Chrysanthemum×morifolium*
Varietal Denomination: Zip

(75) Inventor: Cornelis P. Vandenberg, Fort Myers, FL (US)

(73) Assignee: Yoder Brothers, Inc., Barberton, OH (US)

( * ) Notice: Subject to any disclaimer, the term of this patent is extended or adjusted under 35 U.S.C. 154(b) by 0 days.

(21) Appl. No.: 10/839,163

(22) Filed: May 5, 2004

(51) Int. Cl.[7] ..... A01H 5/00

(52) U.S. Cl. ..... Plt./288

(58) Field of Search ..... Plt./288

*Primary Examiner*—Anne Marie Grunberg
*Assistant Examiner*—June Hwu
(74) *Attorney, Agent, or Firm*—C. A. Whealy

(57) ABSTRACT

A distinct cultivar of *Chrysanthemum* plant named 'Zip', characterized by its upright plant habit; dark green-colored foliage; freely flowering habit; small decorative-type inflorescences that are about 4.1 cm in diameter; attractive white-colored ray florets; response time about 60 days; strong peduncles; and good postproduction longevity with inflorescences and foliage maintaining good substance and color for about two weeks in an interior environment.

2 Drawing Sheets

Botanical classification/cultivar designation: *Chrysanthemum×morifolium* cultivar Zip.

BACKGROUND OF THE INVENTION

The present invention relates to a new and distinct cultivar of *Chrysanthemum* plant, botanically known as *Chrysanthemum×morifolium* and hereinafter referred to by the name 'Zip'.

The new *Chrysanthemum* is a product of a planned breeding program conducted by the Inventor in Salinas, Calif. and Alva, Fla. The objective of the breeding program is to create new cut *Chrysanthemum* cultivars having inflorescences with desirable colors and good inflorescence form and substance.

The new *Chrysanthemum* originated from a cross-pollination made by the Inventor in November, 1994, in Salinas, Calif., of a proprietary *Chrysanthemum×morifolium* seedling selection identified as code number 0715, not patented, as the female, or seed, parent with a proprietary *Chrysanthemum×morifolium* seedling selection identified as 1320, not patented, as the male, or pollen, parent.

The cultivar Zip was discovered and selected by the Inventor as a flowering plant within the progeny of the stated cross-pollination in a controlled environment in Alva, Fla., in November, 2000. The selection of this plant was based on its desirable inflorescence color and good inflorescence form and substance.

Asexual reproduction of the new *Chrysanthemum* by terminal cuttings in a controlled environment in Alva, Fla. since February, 2001, has shown that the unique features of this new *Chrysanthemum* are stable and reproduced true to type in successive generations.

SUMMARY OF THE INVENTION

Plants of the cultivar Zip have not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Zip'. These characteristics in combination distinguish 'Zip' as a new and distinct cultivar:

1. Upright cut *Chrysanthemum* that is usually grown as a natural spray.
2. Dark green-colored foliage.
3. Very freely flowering habit, about eleven inflorescences per flowering stem.
4. Small decorative-type inflorescences that are about 4.1 cm in diameter.
5. Attractive white-colored ray florets.
6. Response time about 60 days.
7. Strong peduncles.
8. Good postproduction longevity with inflorescences and foliage maintaining good substance and color for about two weeks in an interior environment.

Compared to plants of the female parent selection, plants of the new *Chrysanthemum* have slightly larger inflorescences, fewer disc florets per inflorescence and differ in ray floret coloration as plants of the female parent selection have light green-colored ray florets.

Compared to plants of the male parent selection, plants of the new *Chrysanthemum* have fewer disc florets per inflorescence and differ in ray floret coloration as plants of the male parent selection have more green-colored ray florets.

Plants of the new *Chrysanthemum* can be compared to plants of the *Chrysanthemum×morifolium* cultivar Brisa, disclosed in U.S. Plant Pat. No. 9,811. In side-by-side comparisons conducted in Alva, Fla., plants of the new *Chrysanthemum* differed from plants of the cultivar Brisa in the following characteristics:

1. Plants of the new *Chrysanthemum* were more vigorous than plants of the cultivar Brisa.
2. Plants of the new *Chrysanthemum* were more freely flowering than plants of the cultivar Brisa.
3. Plants of the new *Chrysanthemum* flowered about two weeks earlier than plants of the cultivar Brisa.

BRIEF DESCRIPTION OF THE PHOTOGRAPHS

The accompanying colored photographs illustrate the overall appearance of the new *Chrysanthemum,* showing the colors as true as it is reasonably possible to obtain in colored reproductions of this type. Colors in the photographs may differ slightly from the color values cited in the detailed botanical description which accurately describe the colors of the new *Chrysanthemum.*

The photograph on the first sheet comprises a side perspective view of a typical flowering stem of 'Zip' grown as a natural spray.

The photograph on the second sheet comprises a close-up view of a typical flowering stem of 'Zip' grown as a natural spray.

DETAILED BOTANICAL DESCRIPTION

In the following description, color references are made to The Royal Horticultural Society Colour Chart, 1995 Edition, except where general terms of ordinary dictionary significance are used. The aforementioned photographs and following observations and measurements describe plants grown in Madrid, Cundinamarca, Colombia, South America, under conditions which approximate commercial practice in a single-layer polyethylene-covered greenhouse. Two-week old rooted cuttings were planted on Sep. 1, 2003 and received 18 long day/short nights followed by short day/long nights until flowering. Plants were grown as single-stem natural spray cut *Chrysanthemums.* During the production time, the following environmental conditions were measured: day temperatures, 18 to 24° C.; night temperatures, 4 to 12° C.; and light levels, 3,000 to 5,000 foot-candles. Measurements and numerical values represent averages for six to ten typical flowering stems and were taken about nine to ten weeks after the start of short days.

Botanical classification: *Chrysanthemum×morifolium* cultivar Zip.

Commercial classification: Small decorative-type cut *Chrysanthemum.*

Parentage:

*Female or seed parent.*—Proprietary *Chrysanthemum× morifolium* seedling selection identified as code number 0715, not patented.

*Male or pollen parent.*—Proprietary *Chrysanthemum× morifolium* seedling selection identified as code number 1320, not patented.

Propagation:

*Type.*—Terminal tip cuttings.

*Time to rooting.*—About 10 to 14 days with soil temperatures of 18 to 21° C.

*Root description.*—Fine, fibrous; white in color.

*Rooting habit.*—Freely branching.

Plant description:

*Appearance.*—Herbaceous decorative-type cut flower that is typically grown as a natural spray.

*Flowering stem description.*—Aspect: Erect. Length: About 99 cm. Stem diameter: About 8.5 mm. Internode length: About 4.1 cm. Texture: Pubescent; longitudinally ridged. Color: Close to 146A.

*Foliage description.*—Arrangement: Alternate. Length: About 11.1 cm. Width: About 6.5 cm. Apex: Mucronate. Base: Attenuate. Margin: Palmately lobed; sinuses mostly divergent. Texture: Upper and lower surfaces pubescent and leathery; veins prominent on lower surface. Color: Developing foliage, upper surface: Close to 147A. Developing foliage, lower surface: Close to 146B. Fully expanded foliage, upper surface: More green than 147A. Fully expanded foliage, lower surface: Close to 147A. Venation, upper surface: Close to 147B to 146A. Venation, lower surface: Close to 147B. Petiole: Length: About 1.9 cm. Diameter: About 4.5 mm. Color: Upper surface: 147B. Lower surface: Close to 147B.

Flowering description:

*Appearance.*—Small decorative-type inflorescence form with elongated oblong-shaped ray florets. Inflorescences borne on terminals, arising from leaf axils. Disc and ray florets develop acropetally on a capitulum.

*Flowering response.*—Under natural conditions, plant flower in the autumn/winter in the Northern Hemisphere. At other times of the year, inflorescence initiation and development can be induced under short day/long night conditions (at least 13.5 hours of darkness). Plants exposed to two weeks of long day/short night conditions after planting followed by photoinductive short day/long night conditions flower about 60 days later when grown as a natural spray.

*Postproduction longevity.*—In an interior environment, inflorescences and foliage will maintain good color and substance for about two weeks in an interior environment.

*Quantity of inflorescences.*—Very freely flowering habit, about eleven inflorescences per stem develop.

*Inflorescence size.*—Diameter: About 4.1 cm. Depth (height): About 1.7 cm. Diameter of disc: About 2.5 mm. Diameter of receptacle: About 7 mm.

*Inflorescence buds.*—Shape: Oblate. Height: About 6 mm. Diameter: About 7.5 mm. Color: Darker green than 146A.

*Ray florets.*—Shape: Elongated oblong. Surface: Concave. Length: About 1.8 cm. Width: About 6 mm. Corolla tube length: About 5.5 mm. Apex: Rounded to emarginate. Base: Fused. Texture: Smooth, glabrous; satiny; longitudinally ridged. Aspect: Initially upright, eventually perpendicular to peduncle. Number of ray florets per inflorescence: About 165 arranged in numerous rows. Color: When opening, upper and lower surfaces: Close to 154C to 154D. Fully opened, upper and lower surfaces: Close to 155D.

*Disc florets.*—Shape: Tubular, elongated. Length: About 5 mm. Width, apex: About 1.5 mm. Width, base: About 1 mm. Number of disc florets per inflorescence: About five. Color: Immature: Close to 144A. Mature: Apex: Close to 9A. Mid-section: Close to 150D. Base: Close to 155D.

*Phyllaries.*—Quantity per inflorescence: About 22. Length: About 7.5 mm. Width: About 3.5 mm. Shape: Deltoid. Apex: Acute. Base: Truncate. Margin: Entire. Texture, upper surface: Smooth, waxy. Texture: lower surface: Pubescent. Color, upper surface: More green than 146A. Color, lower surface: Darker green than 146A.

*Peduncles.*—Length: First peduncle: About 13 cm. Fourth peduncle: About 17 cm. Seventh peduncle: About 20.5 cm. Diameter: About 3 mm. Angle: About 30° from vertical. Strength: Strong. Texture: Pubescent. Color: Close to 146A.

*Reproductive organs.*—Androecium: Present on disc florets only. Anther color: 9A. Amount of pollen:

None observed. Gynoecium: Present on both ray and disc florets.

*Seed/fruit.*—Seed and fruit production has not been observed.

Disease/pest resistance: Resistance to pathogens and pests common to *Chrysanthemums* has not been observed on plants grown under commercial conditions.

Temperature tolerance: Plants of the new *Chrysanthemum* have demonstrated good tolerance to low temperatures of 4° C. and high temperatures high temperatures of 35° C.

It is claimed:

1. A new and distinct cultivar of *Chrysanthemum* plant named 'Zip', as illustrated and described.

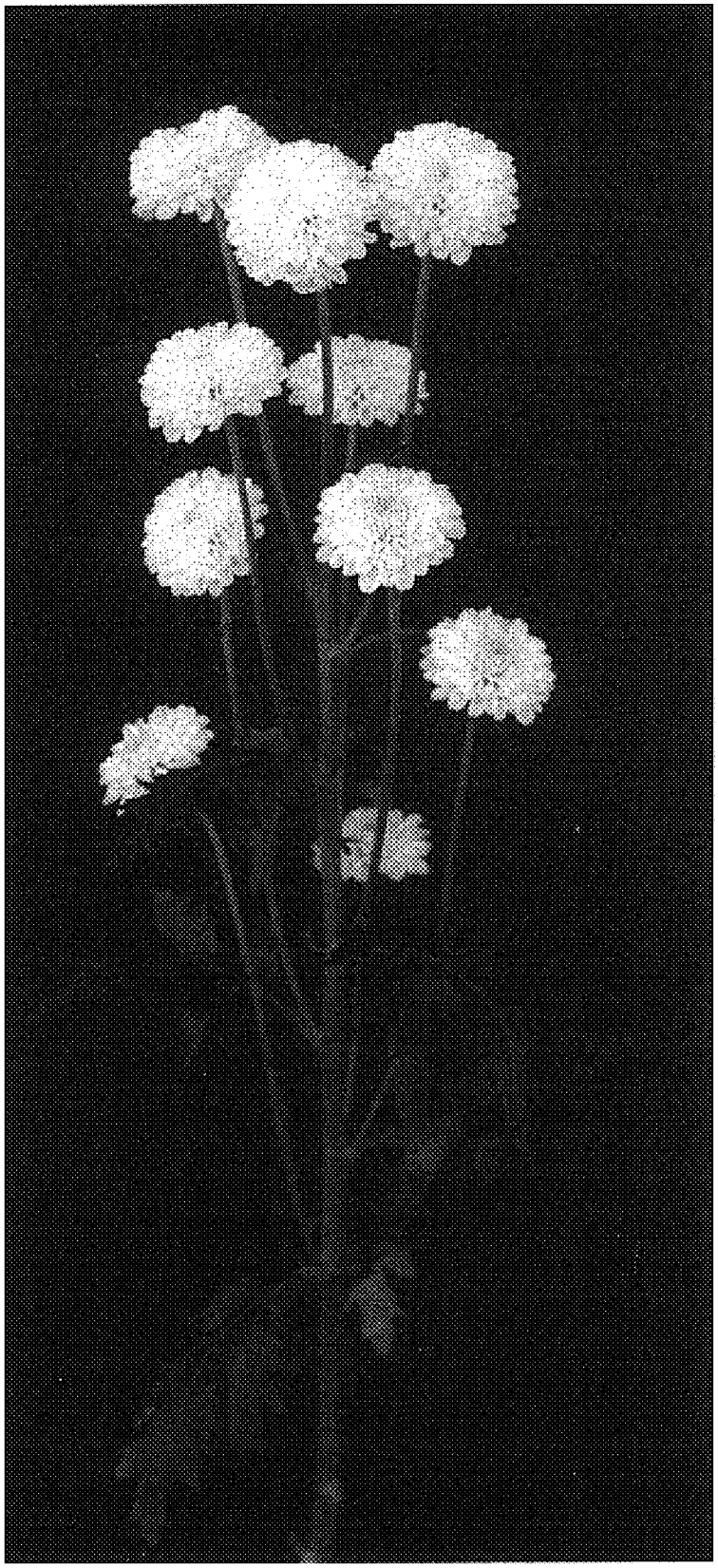

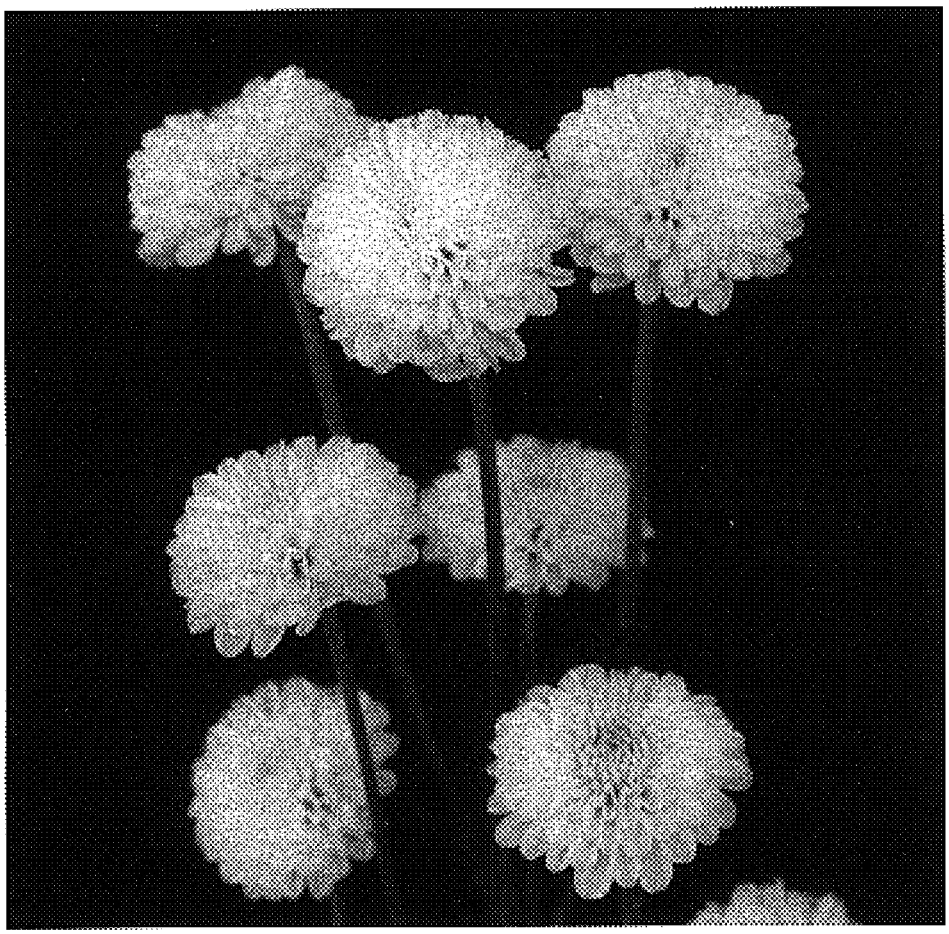

* * * * *